US010133854B2

(12) United States Patent
Campbell et al.

(10) Patent No.: US 10,133,854 B2
(45) Date of Patent: Nov. 20, 2018

(54) COMPOSITIONAL THREE-DIMENSIONAL SURFACE PLOTS

(71) Applicant: International Business Machines Corporation, Armonk, NY (US)

(72) Inventors: Eric J. Campbell, Rochester, MN (US); Sarah K. Czaplewski, Rochester, MN (US)

(73) Assignee: International Business Machines Corporation, Armonk, NY (US)

(*) Notice: Subject to any disclaimer, the term of this patent is extended or adjusted under 35 U.S.C. 154(b) by 3 days.

(21) Appl. No.: 15/153,292

(22) Filed: May 12, 2016

(65) Prior Publication Data

US 2017/0329936 A1  Nov. 16, 2017

(51) Int. Cl.
    *G06T 15/30* (2011.01)
    *G06F 19/00* (2018.01)
    *G06T 17/20* (2006.01)

(52) U.S. Cl.
    CPC .......... *G06F 19/708* (2013.01); *G06T 17/20* (2013.01)

(58) Field of Classification Search
    None
    See application file for complete search history.

(56) References Cited

U.S. PATENT DOCUMENTS 8,014,951 B2   9/2011   Talaalout et al.
8,878,130 B2   11/2014  Inada et al.
2013/0279791 A1   10/2013   Kaizerman et al.
2014/0307066 A1   10/2014   Zhu et al.
2015/0052106 A1   2/2015    Barros
2016/0027200 A1*  1/2016    Corazza ............... G06T 13/40
                                                345/420

FOREIGN PATENT DOCUMENTS

JP    2011127995 A    6/2011
JP    5070074 B2     11/2012

OTHER PUBLICATIONS

Zankel et al., 3D Elemental Mapping in the ESEM—A Combination of Serial Block-face SEM and EDS, Aug. 8, 2011, all pages, URL: http://www.imaging-git.com/science/electron-and-ion-microscopy/3d-elemental-mapping-esem-combination-serial-block-face-sem-and-.*
"Software Extensions for Scandium—the Universal SEM Imaging Platform Scandium" Scandium_Solution_Brochure Olympus Soft Imaging Solutions www.resaltatech.com/resources/brochures/Scandium_Solution.pdf, May 2006, 1 pp.

(Continued)

*Primary Examiner* — Frank Chen
(74) *Attorney, Agent, or Firm* — Patterson + Sheridan, LLP

(57) ABSTRACT

In an example, a method includes receiving, at a computing device, information from a scanning electron microscope (SEM) device. The SEM device includes an energy-dispersive X-ray spectroscopy (EDS) detector, and the information including SEM/EDS data for multiple locations of a sample. The method also includes generating a compositional three-dimensional (3D) surface plot based on the SEM/EDS data. The compositional 3D surface plot includes quantitative atomic composition data for each location of the multiple locations of the sample.

13 Claims, 4 Drawing Sheets

(56) References Cited

OTHER PUBLICATIONS

"Quantax EDS Analysis for SEM and TEM" White Paper Bruker AXS Microanalysis http://www.nanolabtek.com/images/QUANTAX_eng_16page_low_res_01.pdf, 2009, 16 pp.
Burdet, et. al., "Enhanced quantification for 3D SEM—EDS: Using the full set of available X-ray lines" Ultramicroscopy; vol. 148, Jan. 2015, pp. 158-167.
"Anaglyph Maker", "Anaglyph Maker", Stereoeye, http://www.stereoeye.jp/software/index_e.html, 1 page.
"NISTMonte", "NISTMonte", Chemical Science and Technology Laboratory, Surface and Microanalysis Science Division, http://www.cstl.nist.gov/div837/837.02/epq/, 1 page.
"Scandium Solution Height: Take your SEM into the 3rd Dimension", "Scandium Solution Height: Take your SEM into the 3rd Dimension", ResAlta Research Technologies, http://www.resaltatech.com/scandium_sol_height_main.htm#infoarea, 1 page.

\* cited by examiner

COMPOSITIONAL THREE-DIMENSIONAL SURFACE PLOTS

I. FIELD OF THE DISCLOSURE

The present disclosure relates generally to compositional three-dimensional surface plots.

II. BACKGROUND

Energy-dispersive X-ray spectroscopy (EDS) is a method that is used to determine the energy spectrum of X-ray radiation. EDS is an analytical technique that is used for the elemental analysis or chemical characterization of a sample. A conventional EDS map may provide qualitative data which can be difficult to interpret (e.g., when analyzing coatings, mixed materials, etc.).

III. SUMMARY OF THE DISCLOSURE

According to an embodiment, a method includes receiving, at a computing device, information from a scanning electron microscope (SEM) device. The SEM device includes an energy-dispersive X-ray spectroscopy (EDS) detector, and the information including SEM/EDS data for multiple locations of a sample. The method also includes generating a compositional three-dimensional (3D) surface plot based on the SEM/EDS data. The compositional 3D surface plot includes quantitative atomic composition data for each location of the multiple locations of the sample.

According to another embodiment, a computer-readable storage device is disclosed. The computer-readable storage device includes instructions that are executable by a process to perform various operations. The operations include receiving information from an SEM that includes an EDS detector, where the information includes SEM/EDS data for multiple locations of a sample. The method also includes generating a compositional 3D surface plot based on the SEM/EDS data. The compositional 3D surface plot includes quantitative atomic composition data for each location of the multiple locations of the sample.

According to another embodiment, a system is disclosed that includes a processor and a memory in communication with the processor. The memory includes instructions that are executable by the processor to perform various operations. The operations include receiving information from an SEM that includes an EDS detector, where the information includes SEM/EDS data for multiple locations of a sample. The method also includes generating a compositional 3D surface plot based on the SEM/EDS data. The compositional 3D surface plot includes quantitative atomic composition data for each location of the multiple locations of the sample.

One advantage of the present disclosure is the ability to generate a compositional 3D surface plot to enable a user to quantify a composition of a material over an area.

Features and other benefits that characterize embodiments are set forth in the claims annexed hereto and forming a further part hereof. However, for a better understanding of the embodiments, and of the advantages and objectives attained through their use, reference should be made to the Drawings and to the accompanying descriptive matter.

IV. BRIEF DESCRIPTION OF THE DRAWINGS

V. DETAILED DESCRIPTION

Conventional EDS software packages do not include a function that allows a user to generate a three-dimensional (3D) surface plot from EDS hyper map data, spectrum scan data and/or line scan data. A 3D surface plot (where a Z axis is used to represent a nominal atomic or weight percentage and the X and Y axes correspond to a two-dimensional surface being analyzed) would provide additional qualitative and quantitative interpretation of data capable of being collected by an EDS analyzer.

The present disclosure describes a method to generate 3D surface plots from scanning electronic microscope (SEM)/EDS hyper map data. An advantage of generating a 3D surface plot is that the 3D surface plot adds quantitative data to qualitative observations that may be obtained from a traditional hyper map which can improve data interpretation for the user. As further described herein, 3D surface plots can be generated by utilizing data that can be collected from an EDS hyper map or multiple EDS line scans.

A conventional EDS map only provides qualitative data which can be difficult to interpret when analyzing coatings and mixed materials. As an illustrative, non-limiting example, for a sample that includes both palladium (Pd) and gold (Au), one image may correspond to a combined 2D map showing Pd and Au content. Other images may correspond to individual Au and Pd maps. These maps may be difficult to interpret because there are low levels of signal for each element across the entire mapped area. The maps would only be useful qualitatively to determine Au-rich and Pd-rich regions. If a 3D surface plot were generated from the map data, the user would be able to quantify the exact composition of the material.

Unlike other software packages, the present disclosure enables the collection of SEM/EDS data and conversion of that data into a more quantitative compositional 3D surface plot. Thus, unlike other software packages, the objective of the present disclosure is to add quantitative data about elemental atomic percentage to a two-dimensional (2D) EDS element map.

To illustrate, a conventional EDS Monte Carlo simulation software package may be capable of simulating electrons moving through a solid via Monte Carlo simulation. Since this is a simulation software, it does not have the capability of altering and displaying real SEM/EDS data as a compositional 3D surface plot. Another conventional software package may be capable of generating a 3D image of the surface of a sample (i.e., a topographical image) but not generating a compositional 3D surface plot.

Figure 1:
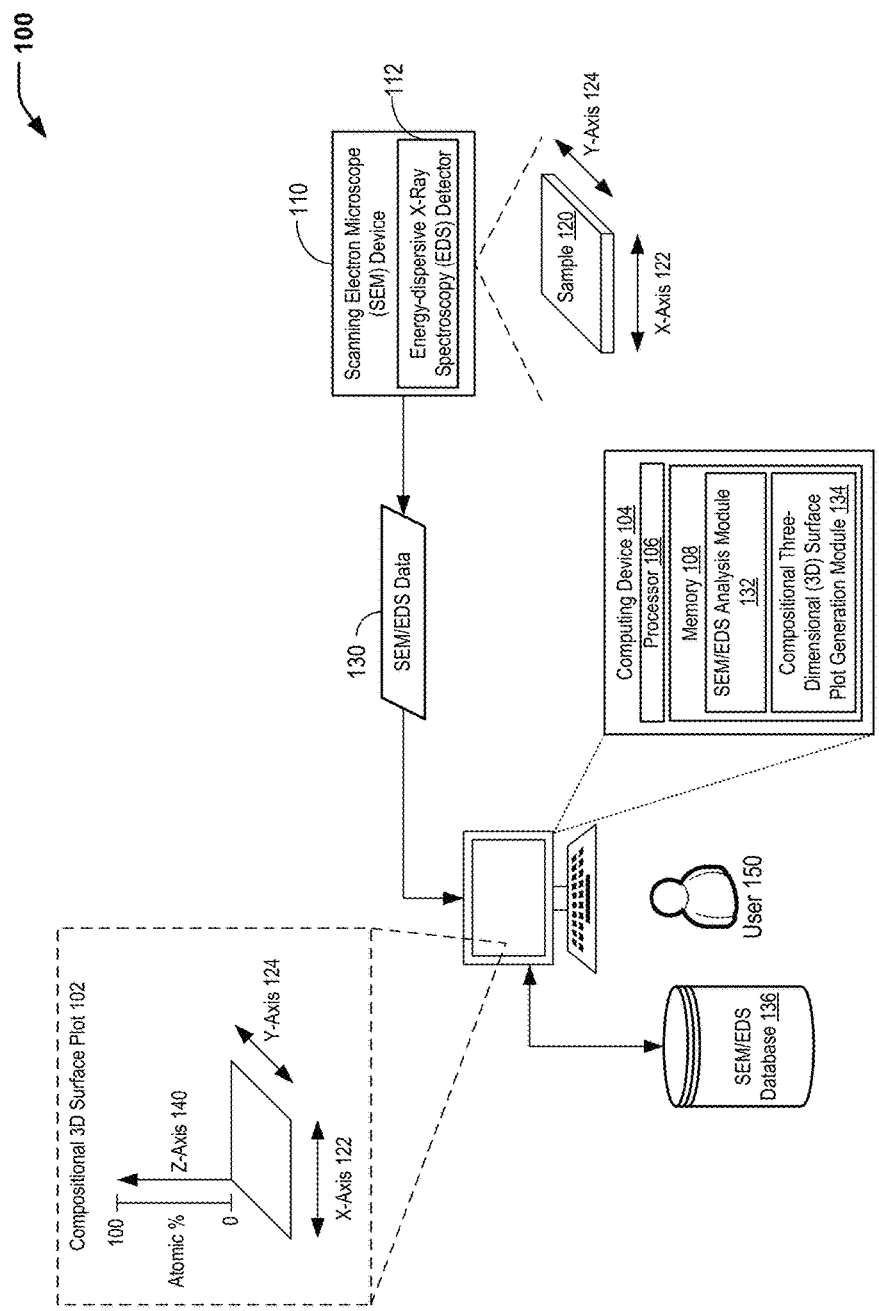
FIG. 1 is a block diagram showing a system for generating a compositional three-dimensional surface plot, according to one embodiment.

FIG. 1 illustrates a particular embodiment of a system 100 for generating a compositional 3D surface plot 102. In FIG. 1, SEM/EDS data is used to generate atomic percentage data at multiple [X, Y] coordinate locations of an analyzed sample and to represent the atomic percentage data along a Z-axis to enable a user to visualize quantitative data for the analyzed sample.

In the example of FIG. 1, the system 100 includes a computing device 104 that includes a processor 106 and a memory 108 in communication with the processor 106. The system 100 further includes an SEM device 110 that is equipped with an EDS detector 112. The SEM device 110 is configured to analyze a sample 120 and to send SEM/EDS data 130 to the computing device 104. FIG. 1 further illustrates an X-axis 122 and a Y-axis 124 of the sample 120. The SEM/EDS data 130 may include SEM/EDS analysis data for multiple [X, Y] coordinates of the sample 120.

In the particular embodiment illustrated in FIG. 1, the memory 108 includes an SEM/EDS analysis module 132 and a compositional 3D surface plot generation module 134. The computing device 104 is configured to receive the SEM/EDS data 130 from the SEM device 110 and (optionally) to store the SEM/EDS data 130 at an SEM/EDS database 136. The SEM/EDS analysis module 132 is configured to analyze the SEM/EDS data 130 to determine an atomic percentage (e.g., weight percentage) at individual [X, Y] coordinates of the sample 120. The compositional 3D surface plot generation module 134 is configured to generate the compositional 3D surface plot 102 based on the atomic percentage data from the SEM/EDS analysis module 132. As shown in the compositional 3D surface plot 102 of FIG. 1, the atomic percentage may be represented along a Z-axis 140. As illustrated and further described herein with respect to FIG. 2, the compositional 3D surface plot 102 of FIG. 1 may enable a user 150 to visualize quantitative compositional information at multiple locations of the sample 120.

Thus, FIG. 1 illustrates an example of a system for generating a compositional 3D surface plot that may enable a user to visualize quantitative data for an analyzed sample at various locations of the analyzed sample.

Figure 2:
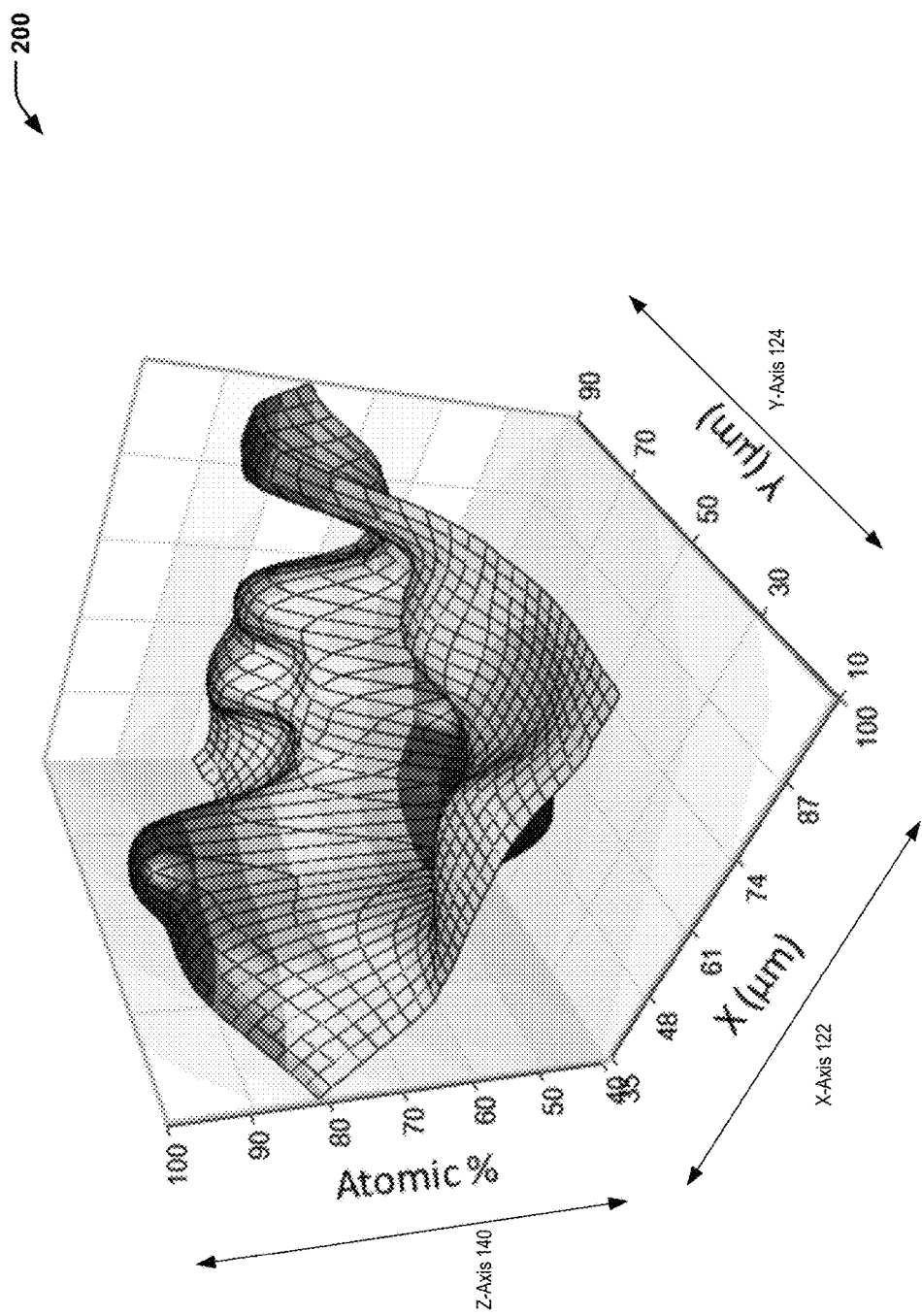
FIG. 2 is a diagram showing an example of a compositional three-dimensional surface plot, according to one embodiment.

FIG. 2 is a diagram 200 depicting an example of a compositional 3D surface plot that could be generated by overlaying a mesh onto a hyper map, according to one embodiment. In a particular embodiment, the compositional 3D surface plot of FIG. 2 may correspond to the compositional 3D surface plot 102 of FIG. 1.

Figure 3:
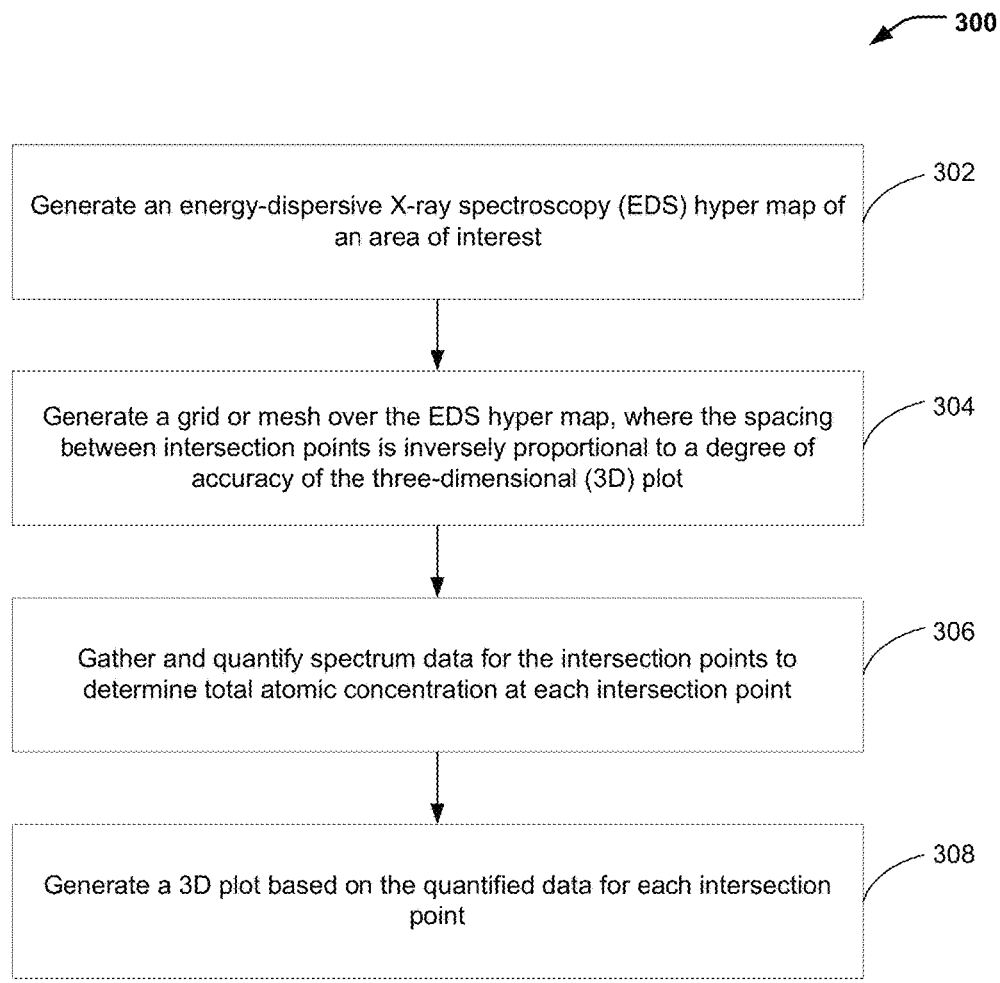
FIG. 3 is a flow diagram showing a particular embodiment of a method of generating a three-dimensional surface plot.

FIG. 3 illustrates a particular embodiment of a method 300 of generating a compositional 3D surface plot. In a particular embodiment, the compositional 3D surface plot may represent an atomic composition (e.g., an atomic weight percentage) to a user along a Z-axis to enable the user to visualize quantitative data for a sample at multiple locations of the sample (as illustrated and further described herein with respect to FIG. 2).

The method 300 includes generating an EDS hyper map of an area of interest, at 302. For example, referring to FIG. 1, the SEM/EDS analysis module 132 may generate an EDS hyper map for an area of interest of the sample 120 based on the SEM/EDS data 130 received from the SEM device 110.

The method 300 includes generating a grid or mesh over the EDS hyper map, at 304. The spacing between intersection points of the grid or mesh is inversely proportional to a degree of accuracy of the 3D plot. For example, referring to FIG. 1, the compositional 3D surface plot generation module 134 may generate a grid or mesh over the EDS hyper map that is generated by the SEM/EDS analysis module 132.

The method 300 includes gathering and quantifying spectrum data for the intersection points to determine the total atomic concentration at each intersection point, at 306. For example, referring to FIG. 1, the compositional 3D surface plot generation module 134 may gather and quantify spectrum data for the intersection points based on the SEM/EDS data 130 to determine the total atomic concentration at each intersection point (e.g., at each intersection point along the X-axis 122 and the Y-axis 124 of the sample 120).

The method 300 includes generating a 3D plot (using a graphing tool) based on the quantified spectrum data of each intersection point, at 308. For example, the compositional 3D surface plot generation module 134 may generate the compositional 3D surface plot 102, with the quantified spectrum data represented along the Z-axis 140.

Figure 4:
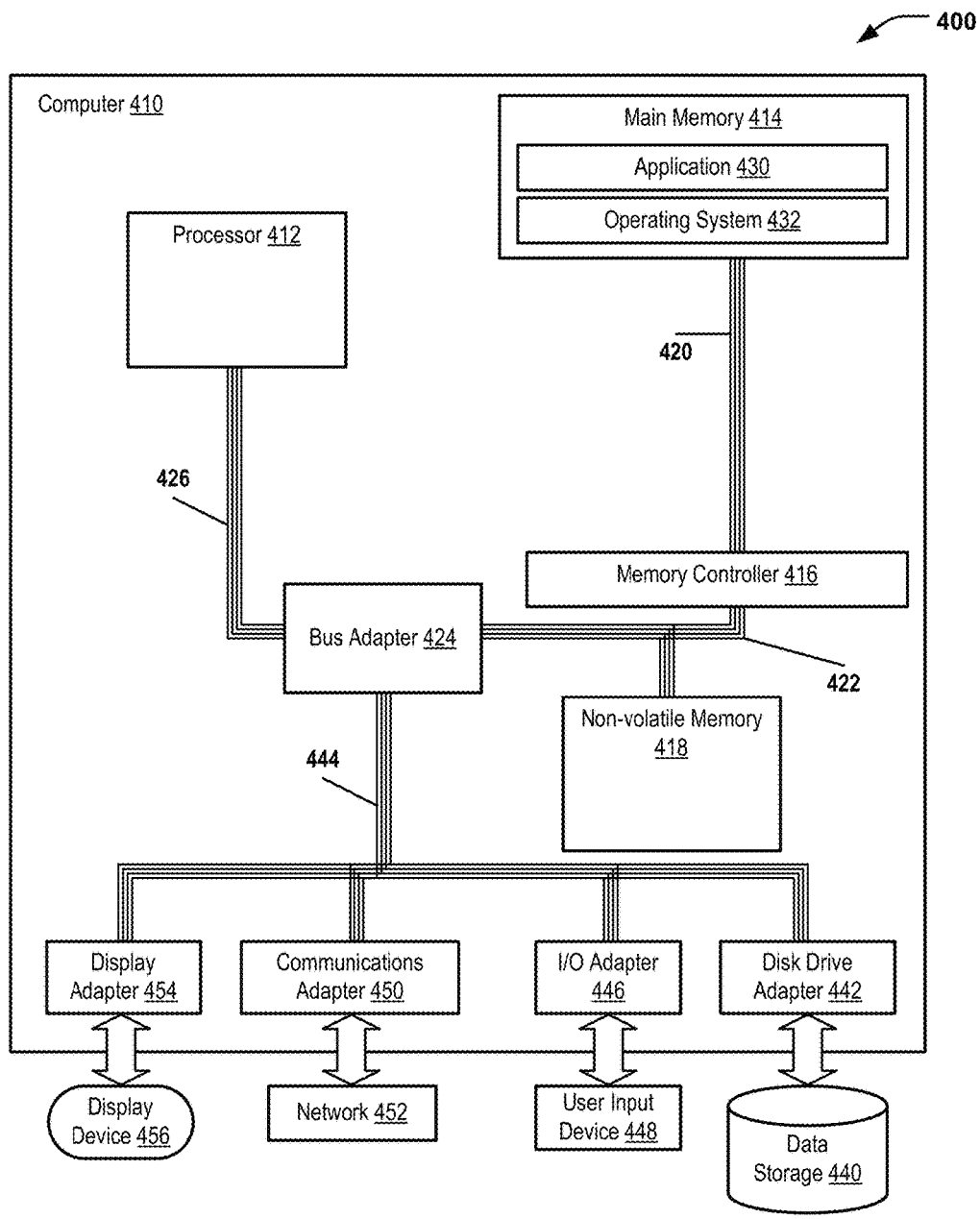
FIG. 4 is a block diagram of an exemplary computer system operable to support embodiments of computer-implemented methods, computer program products, and system components as illustrated in FIGS. 1-3.

Referring to FIG. 4, an exemplary automated computing machinery including a computer 410 is shown. The computer 410 is an exemplary implementation of the computing device 104 of FIG. 1. The computer 410 includes at least one computer processor (CPU) 412 as well as main memory 414, a memory controller 416, and a non-volatile memory 418. The main memory 414 is connected through a memory bus 420 to the memory controller 416. The memory controller 416 and the non-volatile memory 414 are connected through a memory bus 422 and a bus adapter 424 to the processor 412 through a processor bus 426.

Stored at the memory 414 is an application 430 that may be a module of user-level computer program instructions for carrying out particular tasks (e.g., the operations described with respect to the SEM/EDS analysis module 132 and the compositional 3D surface plot generation module 134 of FIG. 1). Also stored at the main memory 414 is an operating system 432. Operating systems include, but are not limited to, UNIX® (a registered trademark of The Open Group), Linux® (a registered trademark of Linus Torvalds), Windows® (a registered trademark of Microsoft Corporation, Redmond, Wash., United States), AIX® (a registered trademark of International Business Machines (IBM) Corp., Armonk, N.Y., United States) i5/OS® (a registered trademark of IBM Corp.), and others as will occur to those of skill in the art. The operating system 432 and the application 430 in the example of FIG. 4 are shown in the main memory 414, but components of the aforementioned software may also, or in addition, be stored at non-volatile memory (e.g., on data storage, such as illustrative data storage 440 and/or the non-volatile memory 418).

The computer 410 includes a disk drive adapter 442 coupled through an expansion bus 444 and the bus adapter 424 to the processor 412 and other components of the computer 410. The disk drive adapter 442 connects non-volatile data storage to the computer 410 in the form of the data storage 440 and may be implemented, for example, using Integrated Drive Electronics ("IDE") adapters, Small Computer System Interface ("SCSI") adapters, Serial Attached SCSI ("SAS") adapters, and others as will occur to those of skill in the art. Non-volatile computer memory also may be implemented as an optical disk drive, electrically erasable programmable read-only memory (so-called "EEPROM" or "Flash" memory), RAM drives, and other devices, as will occur to those of skill in the art.

The computer 410 also includes one or more input/output ("I/O") adapters 446 that implement user-oriented input/output through, for example, software drivers and computer hardware for controlling input and output to and from user input devices 448, such as keyboards and mice. In addition, the computer 410 includes a communications adapter 450 for data communications with a data communications network 452. In a particular embodiment, the communications adapter 450 may be utilized by the computing device 104 of FIG. 1 to communicate with the SEM device 110. As an example, the communications adapter 450 may be utilized by the computing device 104 of FIG. 1 to receive the SEM/EDS data 130 from the SEM device 110.

The data communications may be carried out serially through Recommended Standard 232 (RS-232) connections (sometimes referred to as "serial" connections), through external buses such as a Universal Serial Bus ("USB"), through data communications networks such as internet protocol (IP) data communications networks, and in other ways as will occur to those of skill in the art. The communications adapter 450 implements the hardware level of data communications through which one computer sends data communications to another computer, directly or through a data communications network. Examples of the communications adapter 450 suitable to use in the computer 410 include, but are not limited to, modems for wired dial-up communications, Ethernet (Institute of Electrical and Electronics Engineers (IEEE) 802.3) adapters for wired network communications, and IEEE 802.11 adapters for wireless network communications. The computer 410 also includes a display adapter 454 that facilitates data communication between the bus adapter 424 and a display device 456, enabling the application 430 to visually present output on the display device 456.

Particular embodiments described herein may take the form of an entirely hardware embodiment, an entirely software embodiment, or an embodiment containing both hardware and software elements. In a particular embodiment, the disclosed methods are implemented in software that is embedded in processor readable storage medium and executed by a processor that includes but is not limited to firmware, resident software, microcode, etc.

Further, embodiments of the present disclosure, may take the form of a computer program product accessible from a computer-usable or computer-readable storage medium providing program code for use by or in connection with a computer or any instruction execution system. For the purposes of this description, a computer-usable or computer-readable storage medium can be any apparatus that can tangibly embody a computer program and that can contain, store, communicate, propagate, or transport the program for use by or in connection with the instruction execution system, apparatus, or device.

In various embodiments, the medium can include an electronic, magnetic, optical, electromagnetic, infrared, or semiconductor system (or apparatus or device) or a propagation medium. Examples of a computer-readable storage medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and digital versatile disk (DVD).

A data processing system suitable for storing and/or executing program code may include at least one processor coupled directly or indirectly to memory elements through a system bus. The memory elements can include local memory employed during actual execution of the program code, bulk storage, and cache memories that may provide temporary or more permanent storage of at least some program code in order to reduce the number of times code must be retrieved from bulk storage during execution.

Input/output or I/O devices (including but not limited to keyboards, displays, pointing devices, etc.) can be coupled to the data processing system either directly or through intervening I/O controllers. Network adapters may also be coupled to the data processing system to enable the data processing system to become coupled to other data processing systems or remote printers or storage devices through intervening private or public networks. Modems, cable modems, and Ethernet cards are just a few of the currently available types of network adapters.

The previous description of the disclosed embodiments is provided to enable any person skilled in the art to make or use the disclosed embodiments. Various modifications to these embodiments will be readily apparent to those skilled in the art, and the generic principles defined herein may be applied to other embodiments without departing from the scope of the disclosure. Thus, the present disclosure is not intended to be limited to the embodiments shown herein but is to be accorded the widest scope possible consistent with the principles and features as defined by the following claims.

The invention claimed is:

1. A method comprising:
receiving, at a computing device, information from a scanning electron microscope (SEM) device that includes an energy-dispersive X-ray spectroscopy (EDS) detector, the information including SEM/EDS data for multiple locations of a sample;
generating an EDS hyper map based on the SEM/EDS data; and
overlaying a grid or mesh over the EDS hyper map to generate a compositional three-dimensional (3D) surface plot including quantitative atomic composition data for each location of the multiple locations of the sample, wherein the compositional 3D surface plot includes an X-axis, a Y-axis, and a Z-axis that intersect at a node, wherein the quantitative atomic composition data is represented along the Z-axis, and wherein the X and Y-axes correspond to a two-dimensional (2D) surface comprising the multiple locations of the sample.

2. The method of claim 1, wherein the quantitative atomic composition data includes a weight percentage of a particular atomic element that is present at a particular location of the sample.

3. The method of claim 1, further comprising generating the grid or the mesh.

4. The method of claim 3, further comprising gathering and quantifying spectrum data for intersection points to determine total atomic concentration at each intersection point.

5. The method of claim 4, wherein the compositional 3D surface plot is generated based on the quantified spectrum data for each intersection point.

6. A computer-readable storage device comprising instructions executable by a processor to perform operations including:
receiving information from a scanning electron microscope (SEM) device that includes an energy-dispersive X-ray spectroscopy (EDS) detector, the information including SEM/EDS data for multiple locations of a sample;
generating an EDS hyper map based on the SEM/EDS data; and
overlaying a grid or mesh over the EDS hyper map to generate a compositional three-dimensional (3D) surface plot including quantitative atomic composition data for each location of the multiple locations of the sample, wherein the compositional 3D surface plot includes an X-axis, a Y-axis, and a Z-axis that intersect at a node, wherein the quantitative atomic composition data is represented along the Z-axis, and wherein the X and Y-axes correspond to a two-dimensional (2D) surface comprising the multiple locations of the sample.

7. The computer-readable storage device of claim 6, wherein the quantitative atomic composition data includes a weight percentage of a particular atomic element that is present at a particular location of the sample.

8. The computer-readable storage device of claim 6, wherein the operations further comprise generating the grid or mesh over the EDS hyper map.

9. The computer-readable storage device of claim 8, wherein the operations further comprise gathering and quantifying spectrum data for intersection points to determine total atomic concentration at each intersection point, wherein compositional 3D surface plot is generated based on the quantified spectrum data for each intersection point.

10. A system comprising:
  a processor;
  a memory in communication with the processor, the memory including instructions executable by the processor to perform operations including:
    receiving information from a scanning electron microscope (SEM) device that includes an energy-dispersive X-ray spectroscopy (EDS) detector, the information including SEM/EDS data for multiple locations of a sample;
    generating an EDS hyper map based on the SEM/EDS data; and
    overlaying a grid or mesh over the EDS hyper map to generate a compositional three-dimensional (3D) surface plot including quantitative atomic composition data for each location of the multiple locations of the sample, wherein the compositional 3D surface plot includes an X-axis, a Y-axis, and a Z-axis that intersect at a node, wherein the quantitative atomic composition data is represented along the Z-axis, and wherein the X and Y-axes correspond to a two-dimensional (2D) surface comprising the multiple locations of the sample.

11. The system of claim 10, wherein the quantitative atomic composition data includes a weight percentage of a particular atomic element that is present at a particular location of the sample.

12. The system of claim 10, wherein the operations further comprise; generating the grid or mesh over the EDS hyper map.

13. The system of claim 12, wherein the operations further comprise gathering and quantifying spectrum data for the intersection points to determine total atomic concentration at each intersection point, wherein compositional 3D surface plot is generated based on the quantified spectrum data for each intersection point.

* * * * *